United States Patent
Sauer

(10) Patent No.: US 10,213,269 B2
(45) Date of Patent: Feb. 26, 2019

(54) DEPTH LIMITER FOR SUTURING DEVICES AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 180 days.

(21) Appl. No.: 15/235,858

(22) Filed: Aug. 12, 2016

(65) Prior Publication Data

US 2017/0042629 A1 Feb. 16, 2017

Related U.S. Application Data

(60) Provisional application No. 62/204,852, filed on Aug. 13, 2015.

(51) Int. Cl.
*A61B 17/04* (2006.01)
*A61B 90/00* (2016.01)
*A61B 90/57* (2016.01)

(52) U.S. Cl.
CPC .......... *A61B 90/03* (2016.02); *A61B 17/0469* (2013.01); *A61B 17/0482* (2013.01); *A61B 90/57* (2016.02); *A61B 2090/034* (2016.02); *A61B 2090/062* (2016.02)

(58) Field of Classification Search
CPC . A61B 17/04; A61B 17/0469; A61B 17/0482; A61B 90/00; A61B 90/03; A61F 2/24; A61F 2/2409
See application file for complete search history.

(56) References Cited

U.S. PATENT DOCUMENTS

| | | |
|---|---|---|
| 5,431,666 A | 7/1995 | Sauer |
| 5,562,686 A | 10/1996 | Sauer |
| 5,766,183 A | 6/1998 | Sauer |
| 6,036,641 A * | 3/2000 | Taylor .............. A61B 17/00234 600/229 |
| 6,368,334 B1 | 4/2002 | Sauer |
| 6,533,796 B1 | 3/2003 | Sauer |
| 6,997,931 B2 | 2/2006 | Sauer |
| 7,211,093 B2 | 5/2007 | Sauer |
| 7,407,505 B2 | 8/2008 | Sauer |
| 7,731,727 B2 | 6/2010 | Sauer |
| 8,313,496 B2 | 11/2012 | Sauer |
| 8,398,657 B2 | 3/2013 | Sauer |
| 8,652,149 B2 | 2/2014 | Sauer |
| 2002/0107530 A1 | 8/2002 | Sauer |

(Continued)

OTHER PUBLICATIONS

Jan. 1, 2010 Product Literature; Brown, Charles H, Fast-Fix 360 Meniscal Repair System All Inside Meniscal Repair.

*Primary Examiner* — Victor Nguyen
(74) *Attorney, Agent, or Firm* — Christopher B. Miller

(57) ABSTRACT

A depth limiter for surgical suturing is disclosed. The depth limiter has a tissue stop. The depth limiter also has at least one attachment point coupled to the tissue stop and configured to removably engage a surgical suturing device to position the tissue stop relative to a tissue bite area of the surgical suturing device. A further depth limiter for surgical suturing is disclosed. The depth limiter has a tissue stop. The depth limiter also has at least one attachment point coupled to the tissue stop and configured to engage a surgical suturing device to position the tissue stop relative to a tissue bite area of the surgical suturing device.

14 Claims, 16 Drawing Sheets

(56) References Cited

U.S. PATENT DOCUMENTS

| | | |
|---|---|---|
| 2004/0068272 A1 | 4/2004 | Sauer |
| 2005/0165419 A1 | 7/2005 | Sauer |
| 2009/0222027 A1 | 9/2009 | Sauer |
| 2010/0211083 A1 | 8/2010 | Sauer |
| 2011/0118758 A1 | 5/2011 | Sauer |
| 2012/0016383 A1 | 1/2012 | Sauer |
| 2012/0035623 A1* | 2/2012 | Bagaoisan ......... A61B 17/0057 606/144 |

* cited by examiner

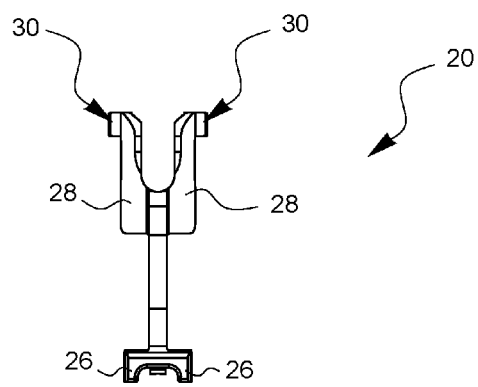
FIG. 2E
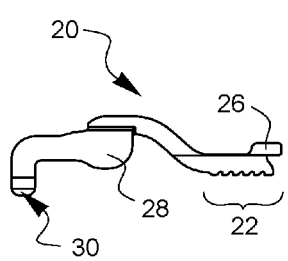
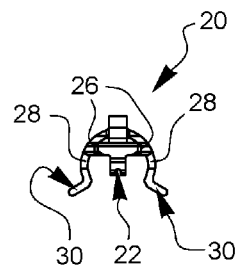
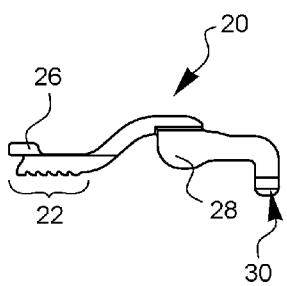
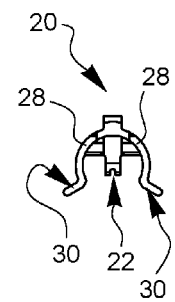
FIG. 2B    FIG. 2A    FIG. 2C    FIG. 2D
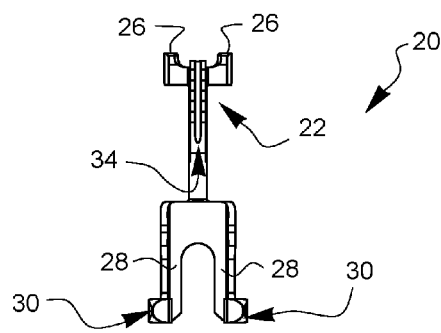
FIG. 2F

DEPTH LIMITER FOR SUTURING DEVICES AND METHODS THEREOF

RELATED APPLICATION

This patent application claims priority to U.S. Provisional Patent Application No. 62/204,852 filed Aug. 13, 2015 and entitled "DEPTH LIMITER FOR SUTURING DEVICES AND METHODS THEREOF". The entire 62/204,852 application is hereby incorporated by reference in its entirety.

FIELD

The claimed invention relates to surgical suturing devices, and more specifically to a depth limiter for surgical suturing.

BACKGROUND

The human heart relies on a series of one-way valves to help control the flow of blood through the chambers of the heart. For example, deoxygenated blood returns to the heart via the superior vena cava and the inferior vena cava, entering the right atrium. The heart muscle tissue contracts in a rhythmic, coordinated heartbeat, first with an atrial contraction which aids blood in the right atrium to pass through the tricuspid valve and into the right ventricle. Following atrial contraction, ventricular contraction occurs and the tricuspid valve closes. Ventricular contraction is stronger than atrial contraction, assisting blood flow through the pulmonic valve, out of the heart via the pulmonary artery, and to the lungs for oxygenation. Following the ventricular contraction, the pulmonic valve closes, preventing the backwards flow of blood from the pulmonary artery into the heart.

Oxygenated blood returns to the heart, via the pulmonary veins, entering the left atrium. Left atrial contraction assists blood in the left atrium to pass through the mitral valve and into the left ventricle. Following the atrial contraction, ensuing ventricular contraction causes mitral valve closure, and pushes oxygenated blood from the left ventricle through the aortic valve and into the aorta where it then circulates throughout the body. Following left ventricular contraction, the aortic valve closes, preventing the backwards flow of blood from the aorta into the heart.

Unfortunately, one or more of a person's heart valves can have or develop problems which adversely affect their function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve prolapses (extends back) into the left atrium during a ventricular contraction. Stenosis, by contrast, is when a heart valve does not fully patent due to stiff or fused leaflets, blood flow tract narrowing, or obstructive material buildup (e.g., calcium). The resultant narrowed outflow causes the heart to work harder to pump blood through it, possibly leading to heart failure.

Fortunately, advances in cardiac surgery, and in particular the evolution of reliable cardio-pulmonary bypass (CPB), have enabled open heart and less-invasive methods for heart valve replacement. During CPB, deoxygenated blood is diverted from the superior vena cava and inferior vena cava in or near the right atrium of the heart, brought outside the body to a CPB machine, reoxygenated, and returned to the body at the aorta, or other great arterial vessels, thereby bypassing the heart and making it possible to stop the heart for cardiac surgery.

Unfortunately, while such cardiac procedures have become common-place, they are not without risks. In particular, extended time on a CPB machine can increase a patient's chances of developing complications involving the inflammatory system, heart, lungs, kidneys, brain, etc. An inflammatory response can be triggered by blood coming into contact with the foreign substances of the tubing leading to the CPB machine and the components of the machine itself. These types of inflammatory responses can damage the endothelium (inner layer of cells) of blood vessels, making them more susceptible to platelet and clot adhesion, and ultimately to an increased chance of atherosclerosis and other cardiovascular complications. Additionally, aortic clamping, necessary to establish the CPB, may cause inadequate blood flow to certain organs, for example, the heart, lungs, kidneys, or brain, thereby leading to possible ischemic damage to those organs. The risks of complications due to CPB increase dramatically with the amount of time a patient is actively connected to the CPB machine. Accordingly, surgeons rely on a combination of specialized skills, knowledge, technologies, and teamwork to operate as efficiently as possible in order to minimize a patient's time on CPB.

Depending on the number of valves being replaced for a patient, a typical heart valve replacement surgery can last between two to six hours, one to two hours of which can be spent on a CPB machine. While the patient is on CPB, the surgeon must gain access to the heart valve, remove the pathologic valve tissue as necessary, and install a replacement valve at the location of the original valve. The valve installation process, typically requiring suture placement and fastening, can be very time consuming, especially when surgeons are operating through small access sites when employing less-invasive techniques to reduce surgical trauma. Furthermore, the suture placements can be in a wide range of different types of tissues. For example, sutures may need to be placed within thin tissues, such as the wall of the aorta, which can be in the neighborhood of 2 mm or less in thickness in the ascending portion, which is often cut to gain access for aortic valve repair or replacement. Once access is gained to the valves and chambers of the heart, however, the tissue to be sutured is much thicker. Currently, surgeons must either have separate suturing devices for different tissue situations or they must try to use a suturing device sized for thicker tissue on thinner tissue by not fully engaging the suturing device with the tissue. In the former case, having multiple suturing devices is very expensive, and in the latter case, it is difficult for the surgeon to partially engage the suturing device with the tissue in a minimally invasive surgical scenario where the surgeon is remotely manipulating the device through a small access incision. Therefore, there is a need for devices and methods which enable surgeons to reliably and efficiently place suture stitches at a variety of tissue depths using a single suturing device. In addition to reducing the cost of surgical procedures, such devices and methods can reduce the amount of time patients need to be attached to a CPB machine, thereby reducing the likelihood of CPB-related side effects. Faster and more reliable cardiac operations offer additional benefits, such as reduced surgical team fatigue and more efficient use of critical resources. Expediting cardiac surgery can also improve patient outcomes.

SUMMARY

A depth limiter for surgical suturing is disclosed. The depth limiter has a tissue stop. The depth limiter also has at least one attachment point coupled to the tissue stop and configured to removably engage a surgical suturing device to position the tissue stop relative to a tissue bite area of the surgical suturing device.

A further depth limiter for surgical suturing is disclosed. The depth limiter has a tissue stop. The depth limiter also has at least one attachment point coupled to the tissue stop and configured to engage a surgical suturing device to position the tissue stop relative to a tissue bite area of the surgical suturing device.

BRIEF DESCRIPTION OF THE DRAWINGS

FIGS. 2A, 2B, 2C, 2D, 2E, and 2F are front, left, right, rear, top, and bottom elevation views of the depth limiter embodiment of FIG. 1A.

Figure 1A:
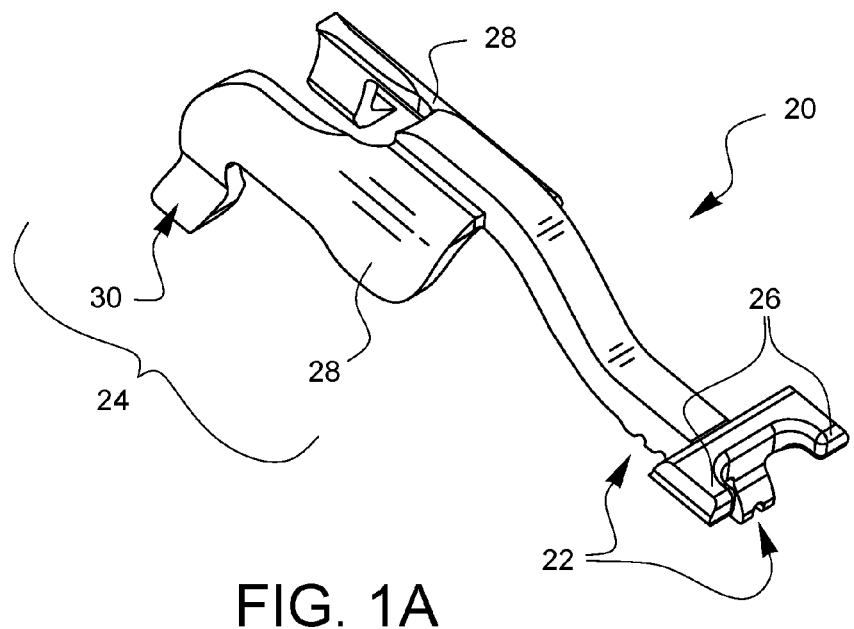
FIG. 1A is a top-left-front perspective view of one embodiment of a depth limiter for surgical suturing.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1B:
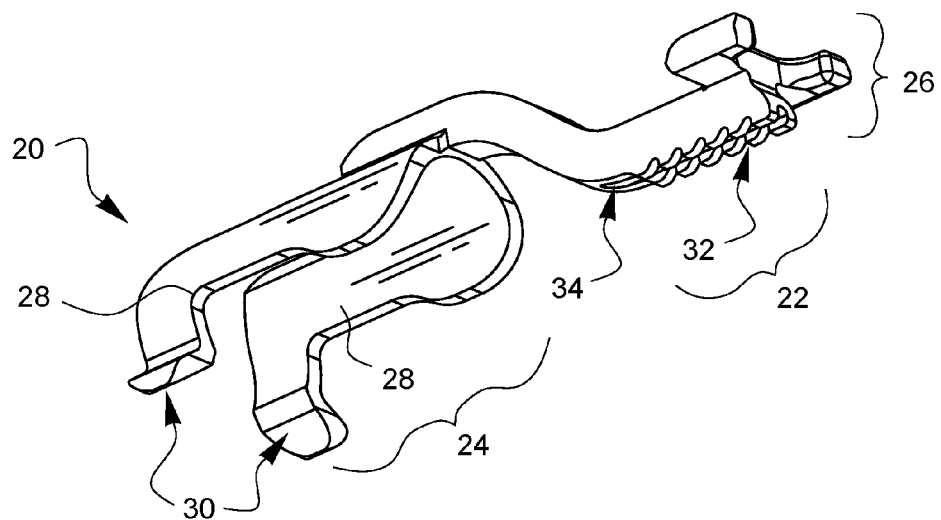
FIG. 1B is a bottom-left-front perspective view of the depth limiter embodiment of FIG. 1A.

FIGS. 1A and 1B are top and bottom perspective views, respectively, of one embodiment of a depth limiter 20 for surgical suturing. The depth limiter 20 has a tissue stop 22. The tissue stop 22 is coupled to and between proximal attachment points 24 and distal attachment points 26. The attachment points 24, 26 are configured to engage a surgical suturing device (none shown in FIGS. 1A and 1B) to position the tissue stop 22 relative to a tissue bite area of the surgical suturing device. Other embodiments may have a lesser or greater number of attachment points. Not all embodiments will have both a proximal and a distal attachment point, and with the teaching of this specification, those skilled in the art will see that other types of attachment points are possible, including an attachment point which is neither proximal nor distal to the tissue stop.

In the embodiment of FIGS. 1A and 1B, the proximal attachment points 24 include opposing shaft clips 28. In this embodiment, the opposing shaft clips 28 are symmetrical, but this does not need to be the case for all embodiments. The shaft clips 28 are sized to engage and hold onto a shaft of a surgical suturing device as will be discussed in more detail with later figures. The shaft clips 28 in this embodiment are configured to engage a round shaft, but other embodiments may be configured to engage any number of different shaft shapes, including, but not limited to square, oval, triangular, and rectangular. Depending on the embodiment, the removal of the depth limiter 20 from a suturing device may be facilitated by one or more release tabs 30 which can be used by a surgeon to pry the depth limiter 20 loose from a surgical suturing device to which it has been attached.

In the embodiment of FIGS. 1A and 1B, the tissue stop 22 has some additional features. In particular, the tissue stop 22 of this embodiment has a tissue grip 32 formed in this example by notches in the tissue stop surface. As will be illustrated in later figures, the tissue stop 22 is designed to come into contact with tissue that is being sutured. If the tissue stop 22 has a tissue grip 32, then the grip 32 may provide some positive control for the surgeon when manipulating the tissue in the tissue bite area in order to have some confidence that the tissue is being held securely in position within the tissue bite area prior to suturing.

The embodied tissue stop 22 of FIGS. 1A and 1B also has a relief channel 34 running down the tissue stop 22 in an axial direction. The tissue which will come into contact with the tissue stop 22 will tend to be slippery from a variety of fluids which may be present in a surgical situation. The relief channel 34 may provide a path for some of the fluids to be evacuated away from the interface of the tissue and the tissue stop 22 when the two surfaces are brought together. This may also help increase the grip and positioning of a suturing device in which the depth limiter has been installed.

FIGS. 2A, 2B, 2C, 2D, 2E, and 2F are front, left side, right side, rear, top, and bottom views, respectively, of the depth limiter 20 of FIGS. 1A and 1B.

Figure 3:
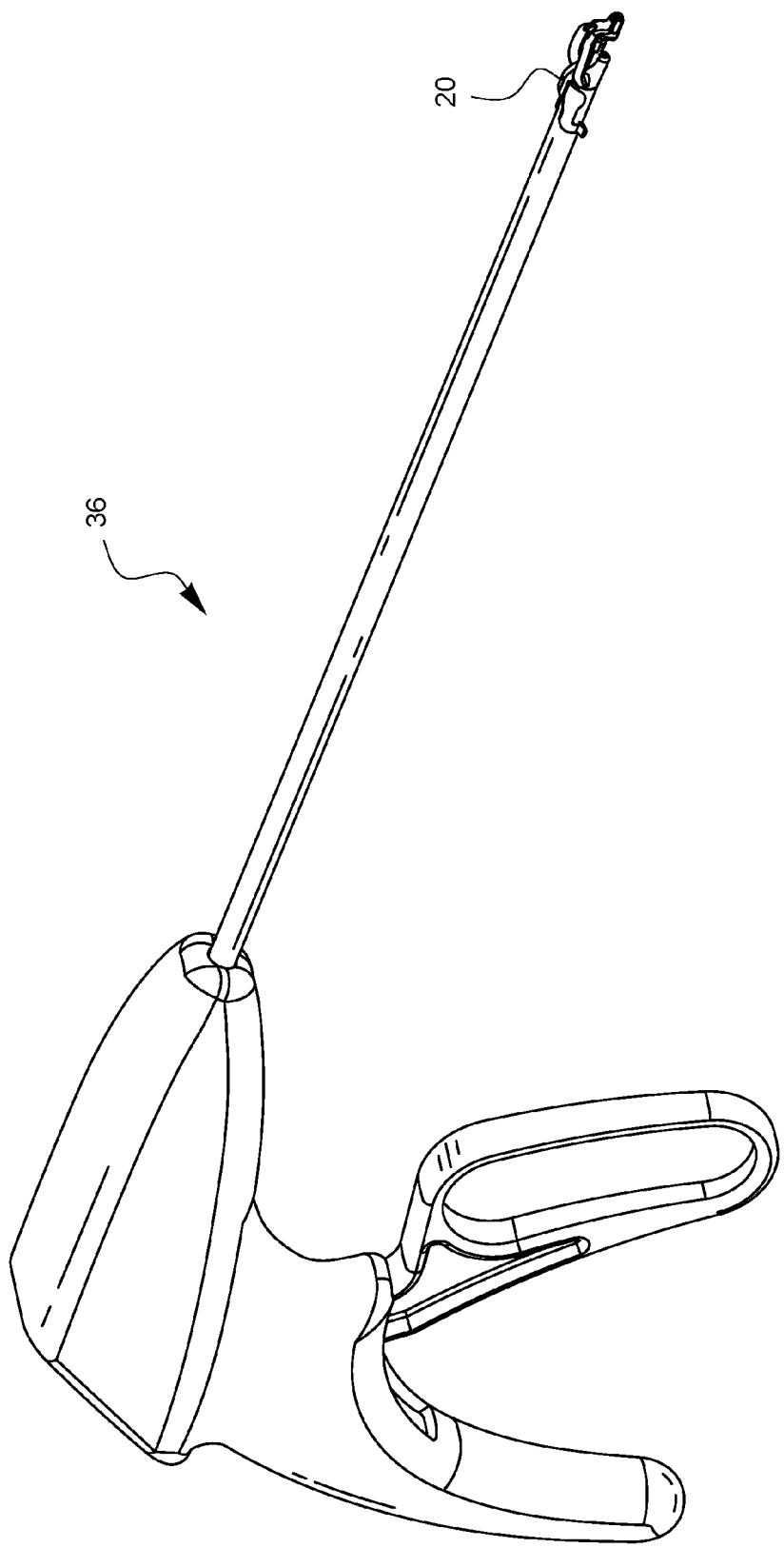
FIG. 3 is a perspective view of one embodiment of a surgical suturing device on which the depth limiter embodiment of FIG. 1A has been attached.

FIG. 3 illustrates the depth limiter 20 of FIGS. 1A and 1B installed on one embodiment of a surgical suturing device 36.

Figure 4A:
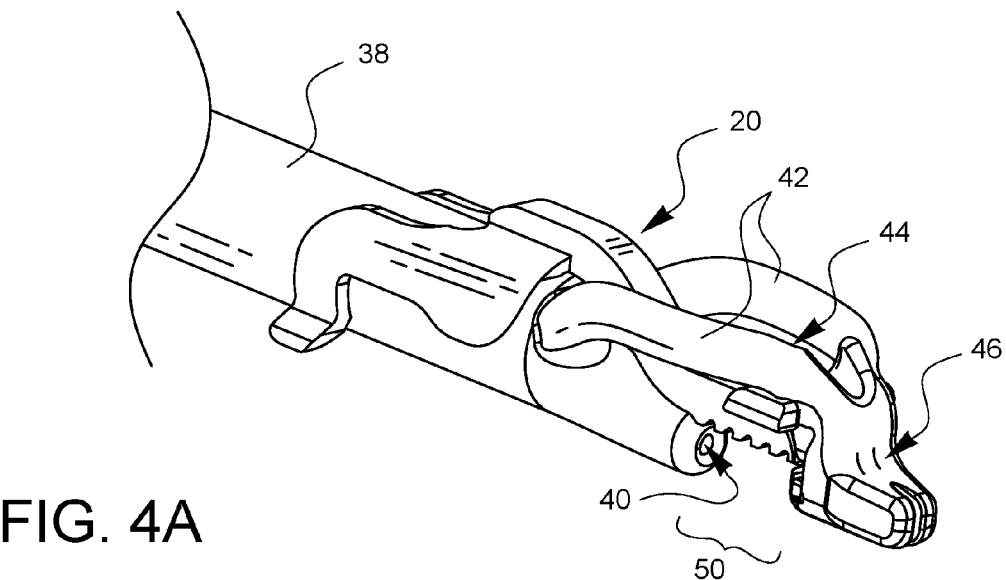
FIGS. 4A and 4B are enlarged perspective views, from top-left-front and bottom-left-rear perspectives, respectively, which show the depth limiter embodiment of FIG. 1A attached onto the distal end of the surgical suturing device embodiment of FIG. 3.
Figure 4B:
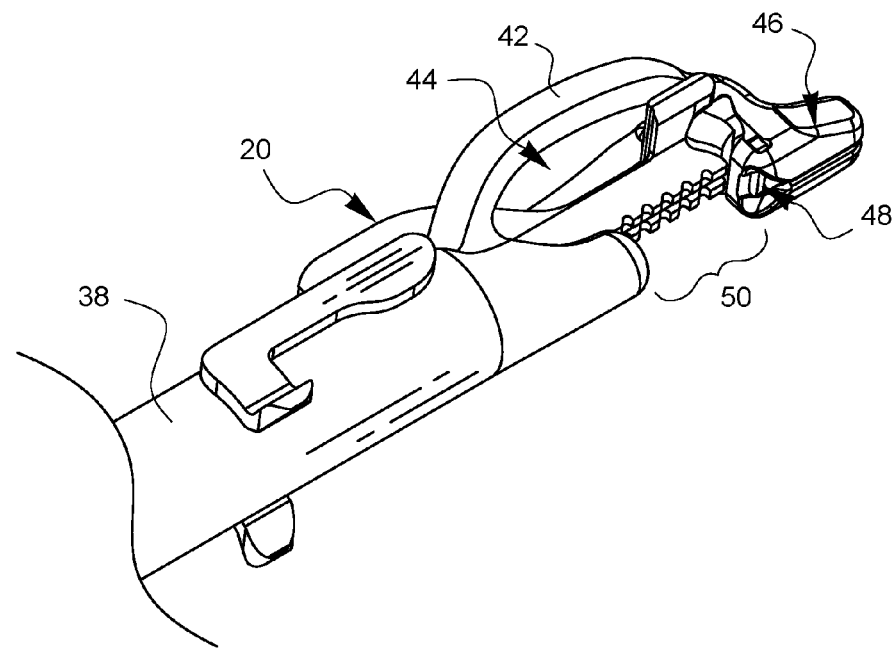

FIGS. 4A and 4B are enlarged top and bottom perspective views, respectively, of the tip of the surgical suturing device from FIG. 3, further illustrating how this embodiment of a depth limiter 20 is attached to the suturing device 36. The suturing device 36 has a shaft 38 which defines a needle exit 40. A needle (not visible in this view) is housed in a retracted position within the shaft 38. Support arms 42 extend from different sides of the shaft 38 to define a viewing port 44 and support a distal end 46. This distal end 46 defines a ferrule holder 48 which can hold a ferrule (not visible in these views) attached to the end of a suture. The ferrule is designed to couple with the needle (also not shown) after the needle exits the needle exit 40, traverses a tissue bite area 50, and enters the ferrule holder 48 to pick up the ferrule.

Figure 5A:
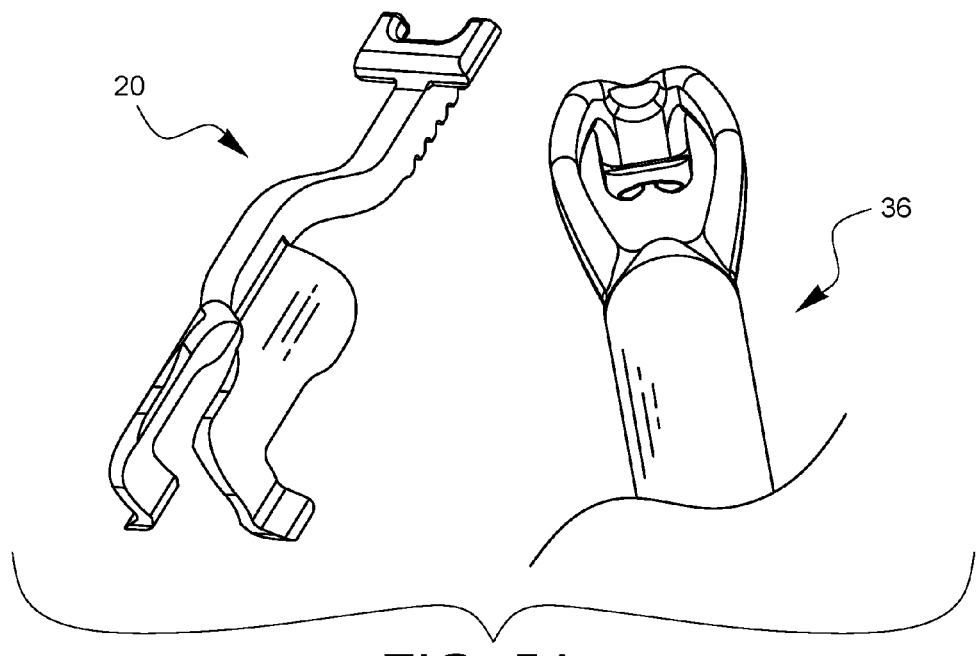
FIGS. 5A-5G illustrate an embodiment of one method for how the depth limiter embodiment of FIG. 1A may be attached to the surgical suturing device embodiment of FIG. 3.
Figure 5B:
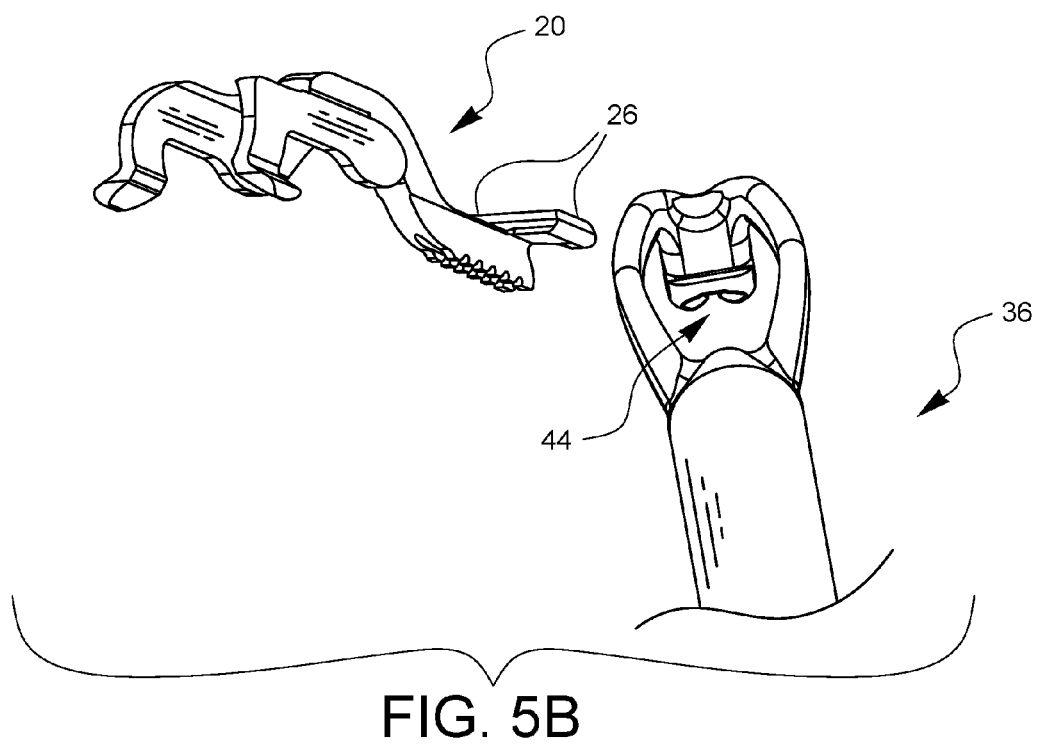
Figure 5C:
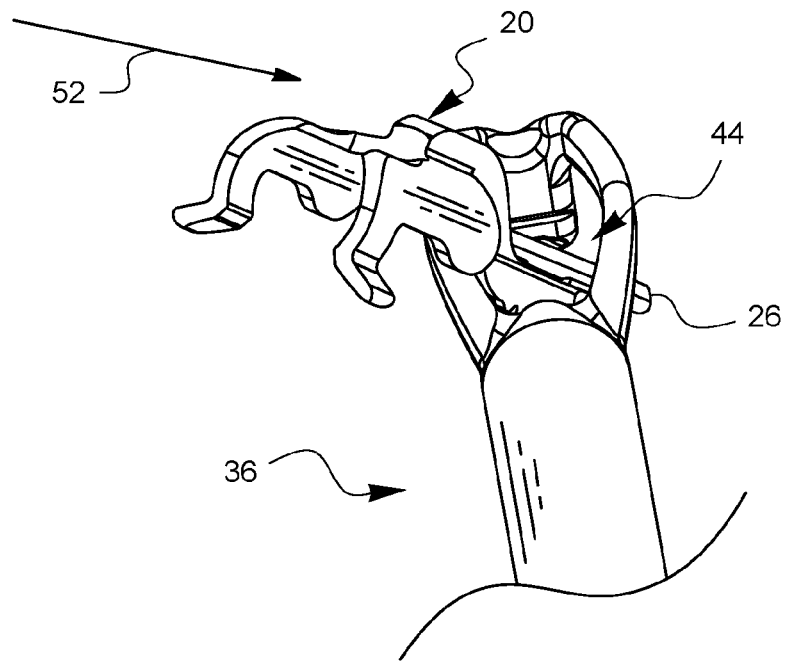
Figure 5D:
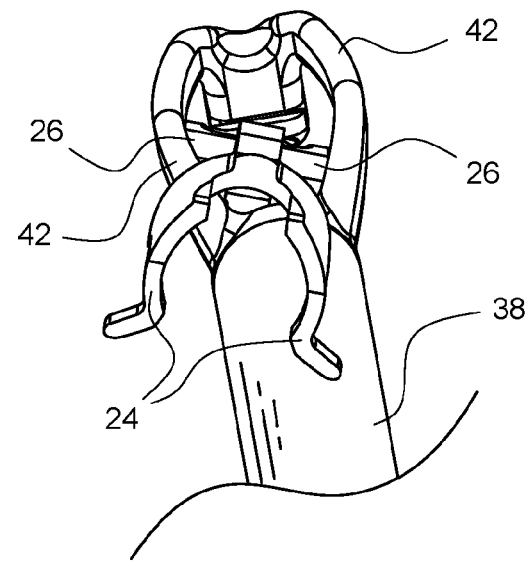
Figure 5E:
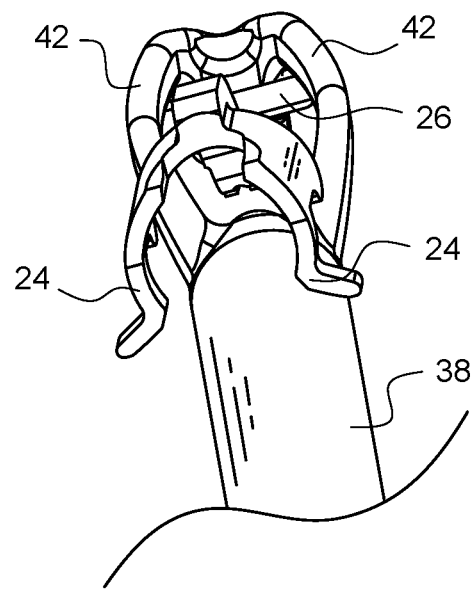
Figure 5F:
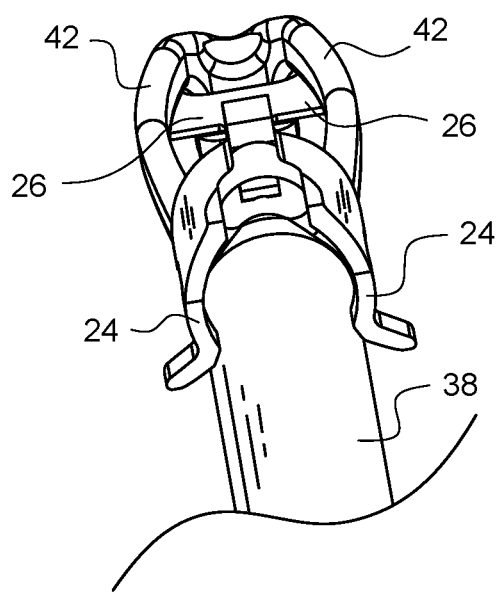
Figure 5G:
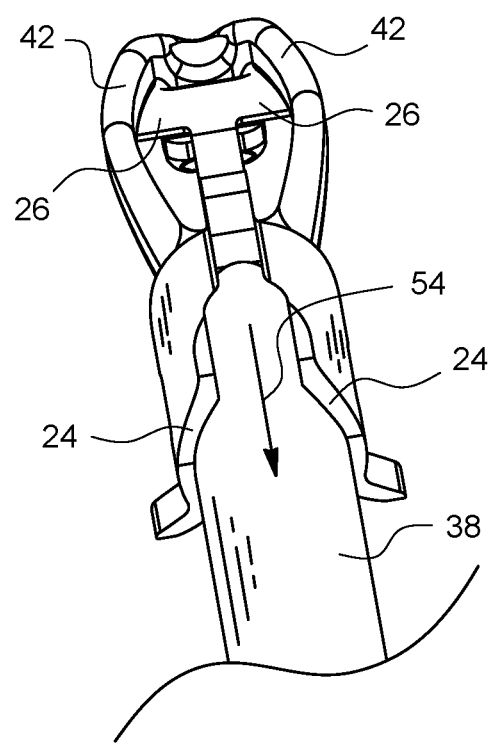

FIGS. 5A-5G illustrate one method for how the depth limiter 20 of the current embodiment may be attached to the surgical suturing device 36. Starting with FIG. 5A, the depth limiter 20 is brought into proximity with the distal end of the suturing device 36. As shown in FIG. 5B, the distal attachment points 26 of the depth limiter 20 are pointed towards the viewing port 44 of the suturing device 36. As shown in FIG. 5C, the depth limiter 20 is moved 52 so the distal attachment points 26 pass through the viewing port 44. As illustrated in FIGS. 5D-5F, the proximal attachment points 24 of the depth limiter 20 are moved into alignment with the top of shaft 38, while the distal attachment points 26 are brought into contact with the bottom of the support arms 42. Finally, in FIG. 5G, the proximal attachment points 24 are pushed down 54 to snap around the shaft 38. The contact of the proximal attachment points 24 with the shaft 38 and the contact of the distal attachment points 26 with the support arms 42 hold the depth limiter 20 in place.

Figure 6A:
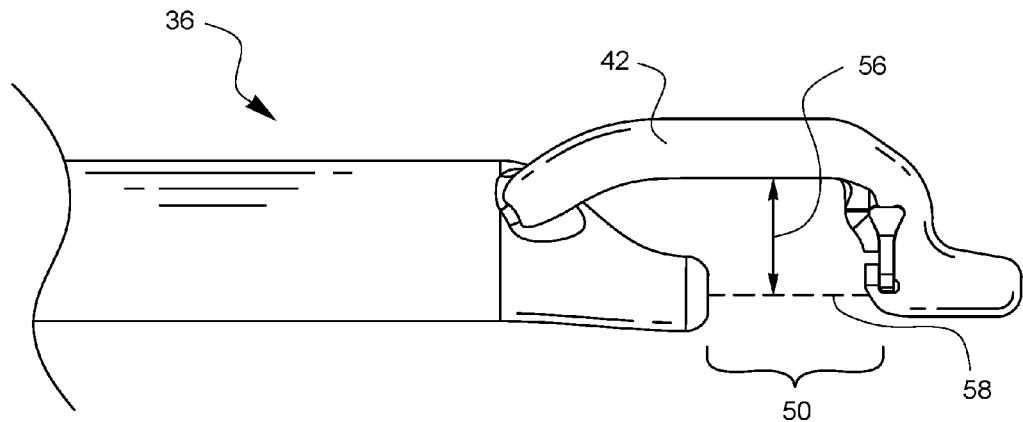
FIGS. 6A and 6B illustrate examples of two different tissue bite depths made possible with the same suturing device when one embodiment of a depth limiter is attached (as in FIG. 6B).
Figure 6B:
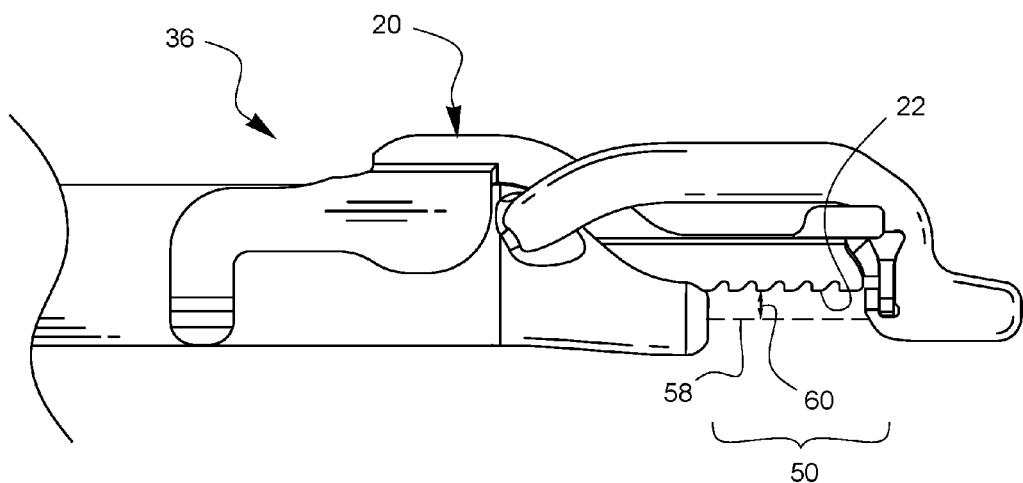

FIGS. 6A and 6B illustrate two different tissue bite depths made possible with the same suturing device 36 when a depth limiter is not installed (as in FIG. 6A) and when a depth limiter 20 is installed (as in FIG. 6B). In FIG. 6A, the tissue bite depth 56 may be measured from an anticipated axis of needle travel 58 up to the bottom of the support arms 42. Such a bite depth 56 may be suitable for thicker tissues. In FIG. 6B, where the depth limiter 20 is installed, an adjusted tissue bite depth 60 may be measured from the anticipated axis of needle travel 58 to the tissue stop 22 of the depth limiter 20. In this way, the depth of the tissue bite may be reduced as desired for thinner tissues.

Figure 6C:
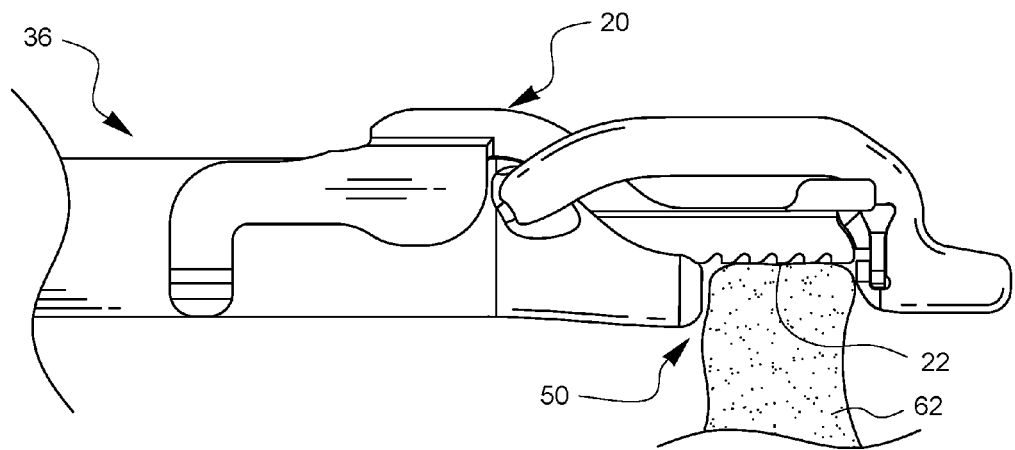
FIG. 6C illustrates a tissue bite area of a surgical suturing device engaging tissue.
Figure 6D:
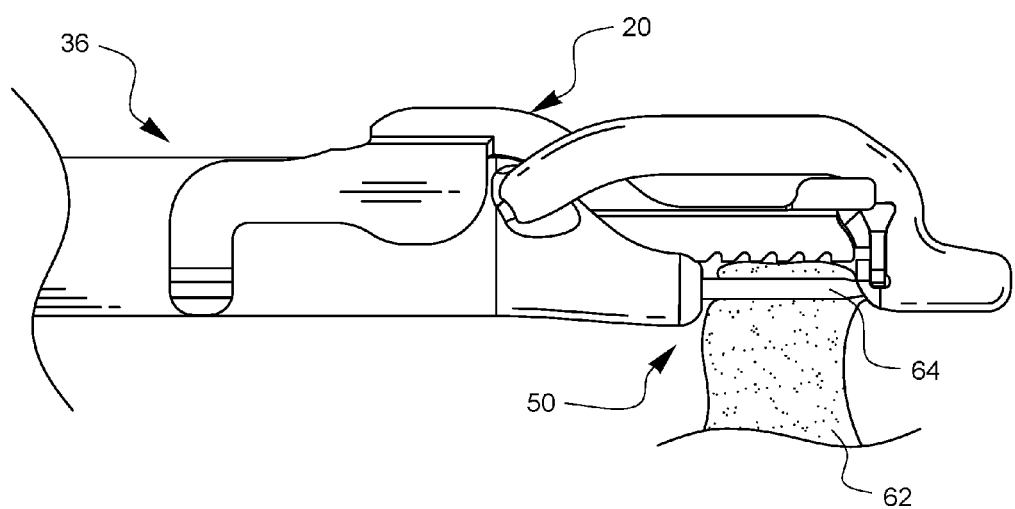
FIG. 6D illustrates the tissue of FIG. 6C being penetrated by a needle from the surgical suturing device at a depth which is controlled by the depth limiter embodiment of FIG. 1A.

FIG. 6C illustrates the tissue bite area 50 of the surgical suturing device 36 being placed over a portion of tissue 62. A depth limiter 20 is installed on the suturing device 36 and the tissue stop 22 controls how far the tissue 62 may enter the tissue bite area 50. FIG. 6D illustrates a needle 64 that has traversed the tissue bite area 50, penetrating the tissue 62 at a limited depth as controlled by the depth limiter 20.

Figure 7A:
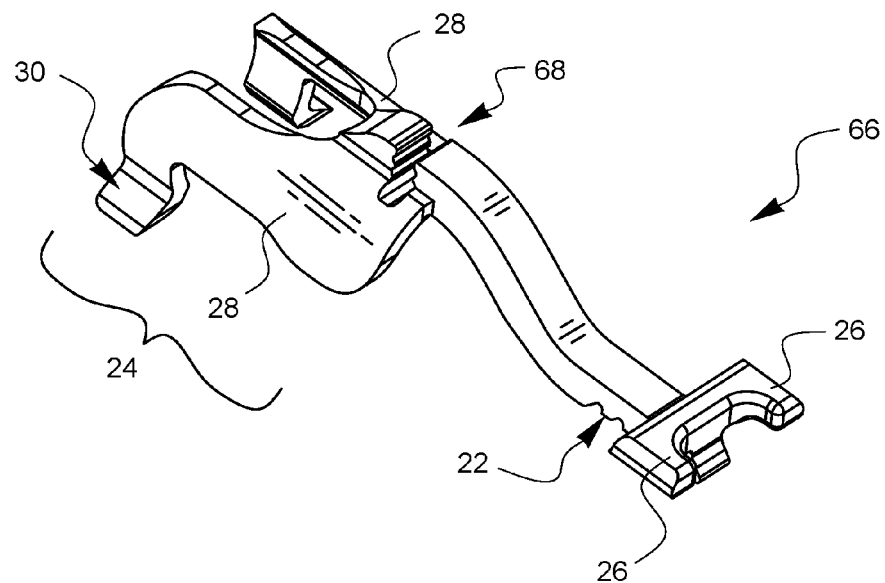
FIGS. 7A and 7B illustrate another embodiment of a depth limiter for surgical suturing in perspective and side views, respectively.
Figure 7B:
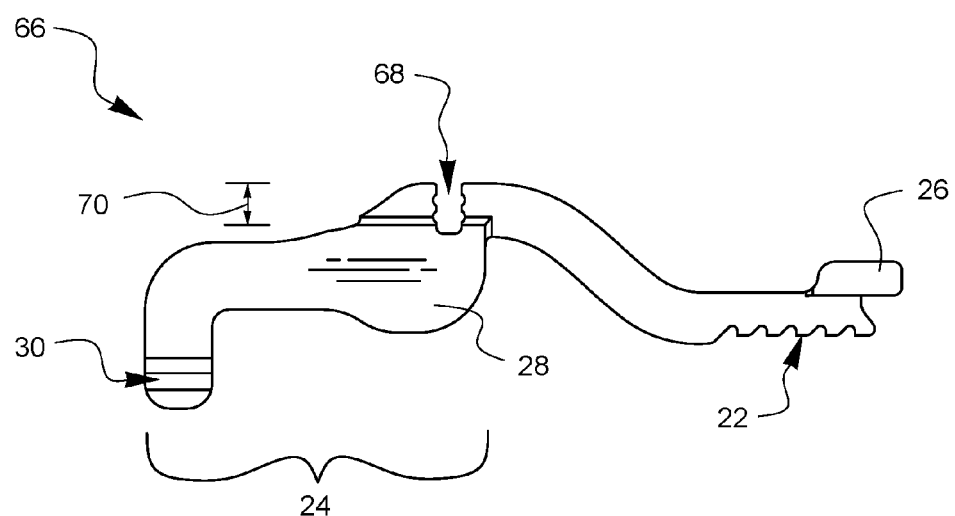

FIGS. 7A and 7B illustrate another embodiment of a depth limiter 66 in perspective and side view, respectively. The embodiment of FIGS. 7A and 7B has all the features of the embodiment of FIGS. 1A and 1B discussed above. However, the embodiment of FIGS. 7A and 7B also has a depth indicator 68. This embodiment of a depth indicator 68 has a depth 70 which is equal to the tissue bite depth that will result from installation of the depth limiter 68 on a corresponding suturing device. Depth limiters may come in different sizes, each limiting a tissue bite to a different depth. A visual cue, such as depth indicator 68, on each specific, different depth limiter can help a surgeon select a suitably sized depth limiter for a desired tissue bite depth based on a set of surgical circumstances. Other embodiments of depth indicators may include words, colors, pictures, symbols, and the like to indicate the anticipated tissue bite depth which would result from a given depth limiter.

Figure 8:
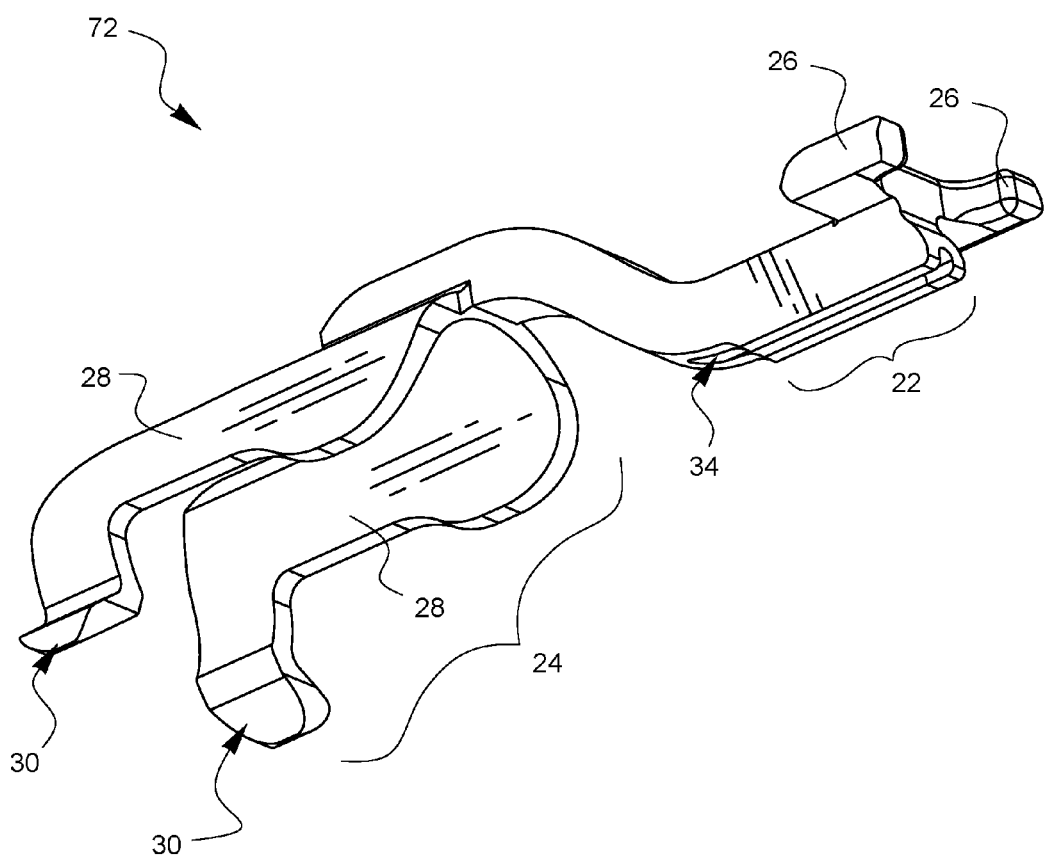
FIG. 8 is a perspective view of a further embodiment of a depth limiter for surgical suturing.

FIG. 8 illustrates a bottom perspective view of a further embodiment of a depth limiter 72. The embodiment of FIG. 8 is similar to the embodiment of FIGS. 1A and 1B discussed above, except that it does not have a tissue grip. Instead, the tissue stop 22 is smooth with only a relief channel 34 passing therethrough.

Figure 9A:
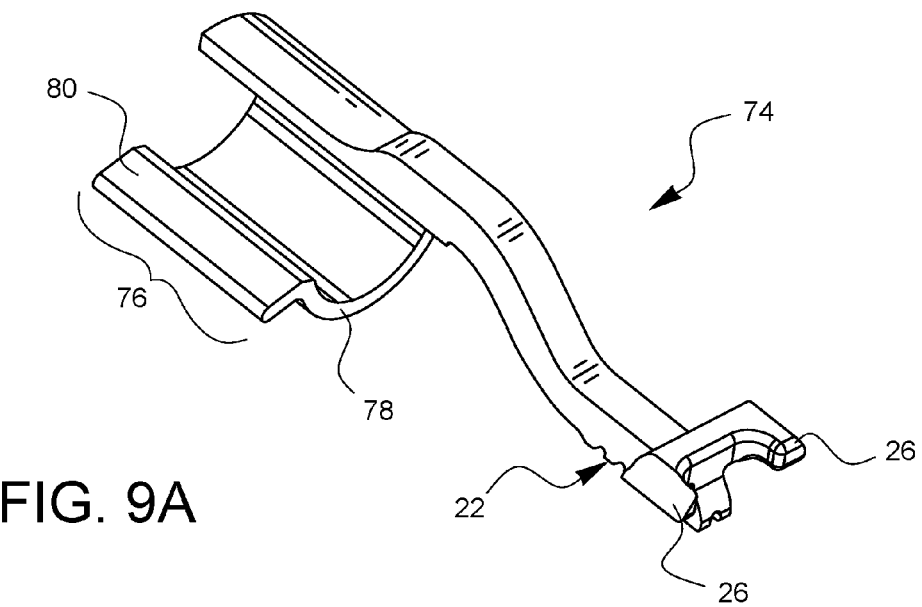
FIG. 9A is a perspective view of another embodiment of a depth limiter for surgical suturing.
Figure 9B:
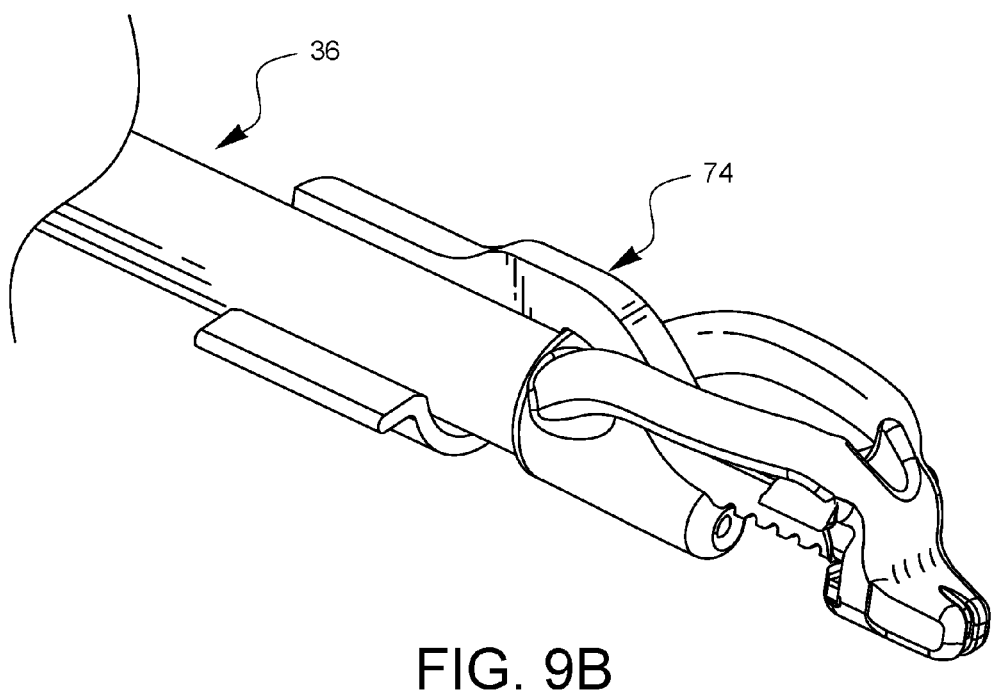
FIG. 9B is a perspective view of the depth limiter embodiment of FIG. 9A attached to one embodiment of a surgical suturing device.

FIG. 9A illustrates a top perspective view of another embodiment of a depth limiter 74. The tissue stop 22 and the distal attachment points 26 are similar to the embodiment of FIGS. 1A and 1B, however, the proximal attachment point 76 is different in this embodiment. The proximal attachment point 76 has a single shaft clip 78 with a single release tab 80. In this embodiment, the shaft clip 78 is configured to extend at least 180 degrees around a shaft of a surgical suturing device which it may engage. As an illustration, FIG. 9B shows the depth limiter 74 of FIG. 9A coupled to a suturing device 36 in a manner similar to those described previously.

Figure 10A:
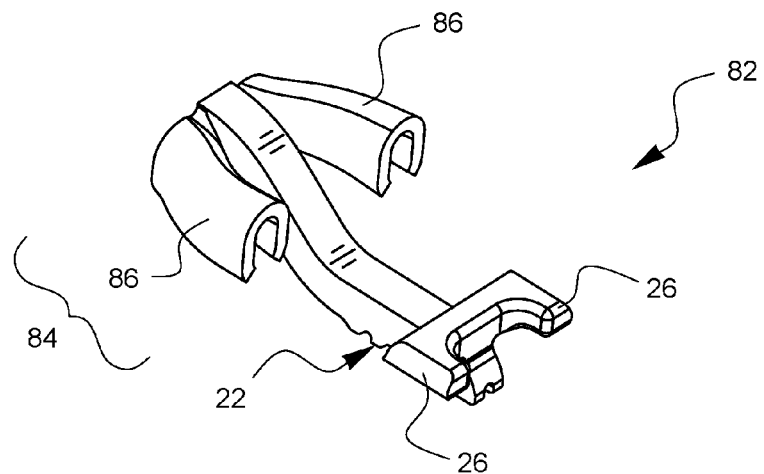
FIG. 10A is a perspective view of a further embodiment of a depth limiter for surgical suturing.
Figure 10B:
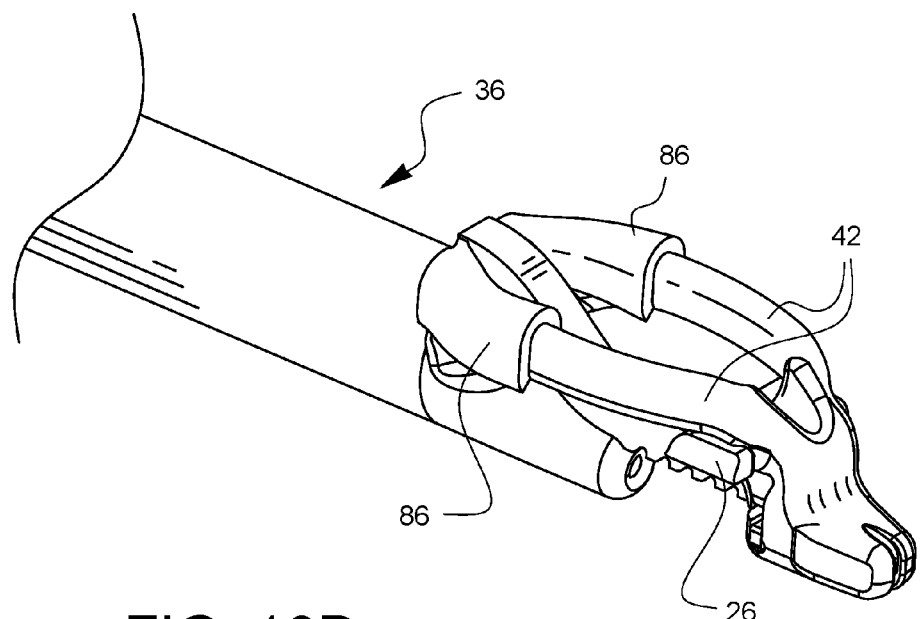
FIG. 10B is a perspective view of the depth limiter embodiment of FIG. 10A attached to one embodiment of a surgical suturing device.

FIG. 10A illustrates a top perspective view of yet another embodiment of a depth limiter 82. The tissue stop 22 and the distal attachment points 26 are similar to the embodiment of FIGS. 1A and 1B, however, the proximal attachment points 84 are different in this embodiment. The proximal attachment points 84 include support arm clips 86 which are configured to engage the support arms 42 of the suturing device 36 as illustrated in FIG. 10B.

Figure 11A:
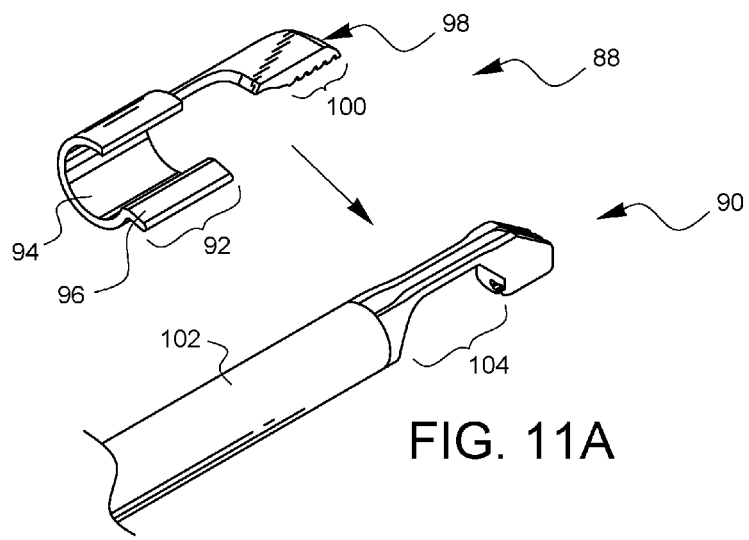
FIG. 11A is a perspective view illustrating another embodiment of a depth limiter for surgical suturing ready to be attached to another embodiment of a surgical suturing device.

FIG. 11A is a perspective view illustrating another embodiment of a depth limiter 88 for surgical suturing ready to be attached to another embodiment of a surgical suturing device 90. The depth limiter 88 has a proximal attachment point 92 which has a single shaft clip 94 with a single release tab 96. The depth limiter 88 also has a distal attachment point 98, and a tissue stop 100. In this embodiment, the shaft clip 94 is configured to extend at least 180 degrees around a shaft 102 of a surgical suturing device 90 which it may engage.

Figure 11B:
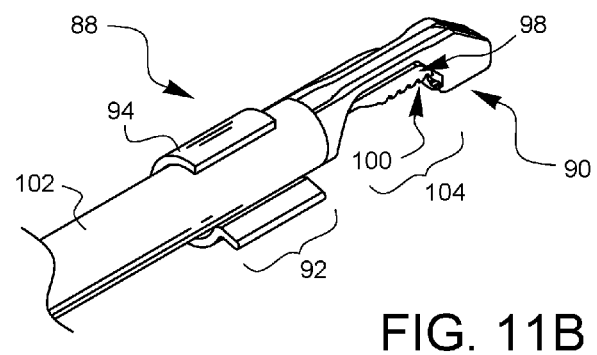
FIG. 11B is a perspective view of the depth limiter embodiment of FIG. 11A attached to the surgical suturing device of FIG. 11A.

FIG. 11B is a perspective view of the depth limiter 88 attached to the surgical suturing device 90. The proximal attachment point 92 is clipped around the shaft 102, while the tissue stop 100 is oriented within a tissue bite area 104 by the distal attachment point 98.

Figure 11C:
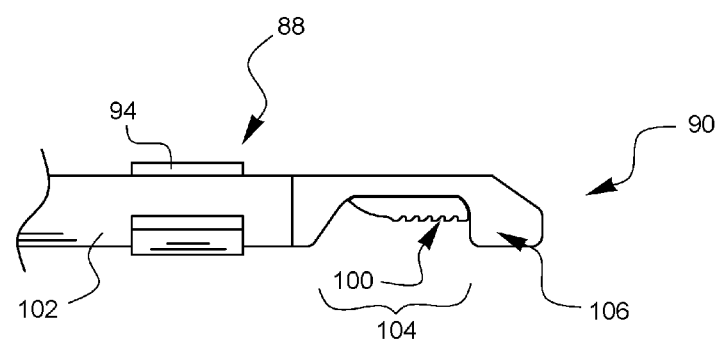
FIG. 11C is a side view of the depth limiter embodiment of FIG. 11A attached to the surgical suturing device of device of FIG. 11A.

FIG. 11C is a side view of the depth limiter 88 attached to the surgical suturing device 90 from FIG. 11B. A needle (not visible in this view) is housed in a retracted position within the shaft 102. The distal end 106 of the surgical suturing device 90 defines a ferrule holder (also not visible in this view, but known to those skilled in the art) which can hold a ferrule attached to the end of a suture. The ferrule is designed to couple with the needle after the needle exits the shaft 102, traverses the tissue bite area 104, and enters the ferrule holder on the distal end 106 to pick up the ferrule. As can be seen from the side view of FIG. 11C, the tissue stop 100 of the depth limiter 88 fills a portion of the tissue bite area 104, thereby limiting how much tissue can fit into the tissue bite area and how deeply the needle can traverse within the tissue.

Figure 12A:
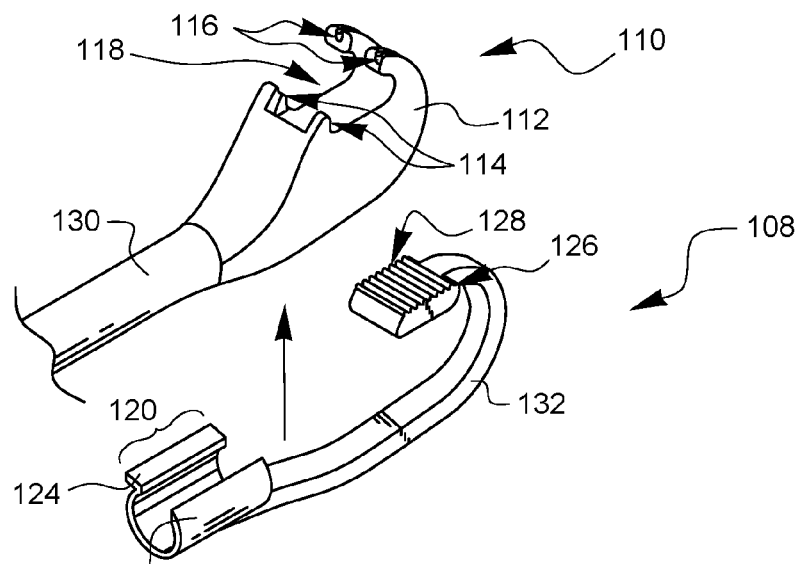
FIG. 12A is a perspective view illustrating a further embodiment of a depth limiter for surgical suturing ready to be attached to a further embodiment of a surgical suturing device.

FIG. 12A is a perspective view illustrating another embodiment of a depth limiter 108 for surgical suturing ready to be attached to another embodiment of a surgical suturing device 110. This embodiment of a surgical suturing device 110 has a pair of arcuate needle arms (not visible in this view) which are housed within the distal tip 112. The needle arms may be rotated to exit through ports 114 on an arcuate path towards corresponding ferrule holders 116. While the arcuate needles move from the exit ports 114 to the ferrule holders 116, they traverse a tissue bite area 118.

In the embodiment of FIG. 12A, the depth limiter 108 has a proximal attachment point 120 which has a single shaft clip 122 with a single release tab 124. The depth limiter 108 also has a distal attachment point 126, and a tissue stop 128. In this embodiment, the shaft clip 122 is configured to extend at least 180 degrees around a shaft 130 of a surgical suturing device 110 which it may engage. The tissue stop 128 is coupled to the proximal attachment 120 by a flexible link 132.

Figure 12B:
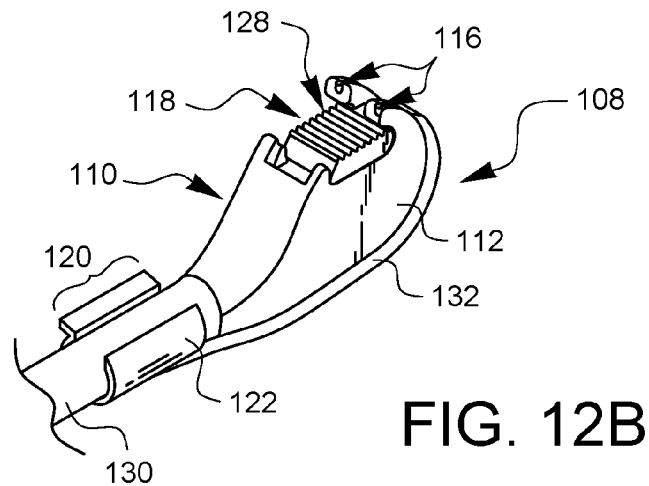
FIG. 12B is a perspective view of the depth limiter embodiment of FIG. 12A attached to the surgical suturing device of FIG. 12A.

FIG. 12B is a perspective view of the depth limiter 108 attached to the surgical suturing device 110. The flexible link 132 is flexed to allow the tissue stop 128 to sit within the tissue bite area 118 while the flexible link 132 is settled between the ferrule holders 116, and then routed along the bottom of the distal tip 112 so the proximal attachment point 120 can be clipped around the shaft 130.

Figure 12C:
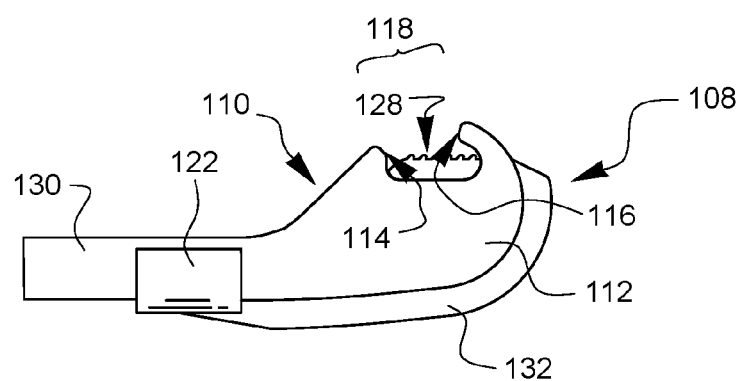
FIG. 12C is a side view of the depth limiter embodiment of FIG. 12A attached to the surgical suturing device of device of FIG. 12A.

FIG. 12C is a side view of the depth limiter 108 attached to the surgical suturing device 110 from FIG. 12B. As mentioned previously, the suturing device 110 has a pair of arcuate needle arms (not visible in this view) which are housed within the distal tip 112. The needle arms may be rotated to exit through ports 114 on an arcuate path towards corresponding ferrule holders 116. While the arcuate needles move from the exit ports 114 to the ferrule holders 116, they traverse a tissue bite area 118. As is known to those skilled in the art, the ferrule holders 116 can each hold a ferrule attached to the end of a suture. Each ferrule is designed to couple with a respective arcuate needle arm after the needle arm exits the port 114, traverses the tissue bite area 118, and enters the ferrule holder 116 to pick up the ferrule. As can be seen from the side view of FIG. 12C, the tissue stop 128 of the depth limiter 108 fills a portion of the tissue bite area 118, thereby limiting how much tissue can fit into the tissue bite area and how deeply the needle can traverse within the tissue.

Various advantages of a depth limiter for surgical suturing have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A depth limiter for surgical suturing, comprising:
    a tissue stop;
    at least one attachment point coupled to the tissue stop and configured to removably engage a surgical suturing device to position the tissue stop relative to a tissue bite area of the surgical suturing device;
    wherein the at least one attachment point comprises a shaft clip; and
    the shaft clip is configured to extend at least 180 degrees around a shaft of the surgical suturing device which the at least one attachment point is configured to removably engage.

2. The depth limiter of claim 1, wherein the tissue stop comprises a tissue grip.

3. The depth limiter of claim 1, wherein the tissue stop comprises a shape configured to be substantially parallel to a travel path of a suturing needle of the suturing device which the at least one attachment point is configured to engage.

4. The depth limiter of claim 1, wherein the tissue stop comprises a relief channel.

5. The depth limiter of claim 1, further comprising a depth indicator.

6. The depth limiter of claim 1, wherein the at least one attachment point comprises a pair of opposing shaft clips.

7. The depth limiter of claim 6, wherein each of the opposing shaft clips is symmetrical with the other.

8. The depth limiter of claim 1, wherein the at least one attachment point coupled to the tissue stop comprises a release tab.

9. The depth limiter of claim 1, wherein the at least one attachment point comprises a support arm brace.

10. The depth limiter of claim 1, wherein the at least one attachment point comprises an attachment point proximal to the tissue stop.

11. The depth limiter of claim 1, wherein the at least one attachment point comprises an attachment point distal to the tissue stop.

12. The depth limiter of claim 1, wherein the at least one attachment point comprises:
    a first attachment point proximal to the tissue stop; and
    a second attachment point distal to the tissue stop.

13. The depth limiter of claim 1, wherein the tissue stop is coupled to the at least one attachment point such that when the tissue stop is positioned relative to the tissue bite area of the surgical suturing device, the tissue stop is positioned adjacent a travel path of a suturing needle of the surgical suturing device which it is configured to engage.

14. The depth limiter of claim 13, wherein the tissue stop is positioned substantially parallel to the travel path of the suturing needle of the surgical suturing device which it is configured to engage.

* * * * *